(12) United States Patent
Nakaji (10) Patent No.: US 11,298,008 B2
(45) Date of Patent: Apr. 12, 2022

(54) BENDING PORTION OF ENDOSCOPE AND ENDOSCOPE

(71) Applicant: OLYMPUS CORPORATION, Tokyo (JP)

(72) Inventor: Hiroaki Nakaji, Nagoya (JP)

(73) Assignee: OLYMPUS CORPORATION, Tokyo (JP)

( * ) Notice: Subject to any disclaimer, the term of this patent is extended or adjusted under 35 U.S.C. 154(b) by 353 days.

(21) Appl. No.: 16/529,996

(22) Filed: Aug. 2, 2019

(65) Prior Publication Data

US 2020/0000312 A1 Jan. 2, 2020

Related U.S. Application Data

(63) Continuation of application No. PCT/JP2017/033405, filed on Sep. 15, 2017.

(30) Foreign Application Priority Data

Feb. 20, 2017 (JP) .............................. JP2017-028775

(51) Int. Cl.
*A61B 1/00* (2006.01)
*A61B 1/008* (2006.01)
(Continued)

(52) U.S. Cl.
CPC ............ *A61B 1/008* (2013.01); *A61B 1/0057* (2013.01); *A61B 1/00114* (2013.01);
(Continued)

(58) Field of Classification Search
None
See application file for complete search history.

(56) References Cited

U.S. PATENT DOCUMENTS 5,178,129 A * 1/1993 Chikama .............. A61B 1/0051 138/120
2002/0032371 A1* 3/2002 Torii .................... A61B 1/0052 600/142

(Continued)

FOREIGN PATENT DOCUMENTS

| JP | 2003-126024 A | 5/2003 | |
| JP | 2005-007068 A | 1/2005 | |
| JP | 2005007068 A * | 1/2005 | ........... A61B 1/0055 |

OTHER PUBLICATIONS

International Search Report dated Nov. 7, 2017 received in PCT/JP2017/033405.

*Primary Examiner* — Timothy J Neal
(74) *Attorney, Agent, or Firm* — Scully, Scott, Murphy & Presser, P.C.

(57) ABSTRACT

A bending portion includes: a bending piece group including a plurality of first bending pieces; and a second bending piece including coupling protruding portions for coupling to a coupling frame so as to resist torsion about the longitudinal axis, and including, on a proximal end side, third contact surfaces facing a direction of the longitudinal axis, the second bending piece including inside a second insertion portion for allowing insertion of internal components, the second insertion portion being formed so as to be coincident with the first insertion portion provided in each of the first bending pieces on a same projection plane, the second bending piece being interposed between the coupling frame and the bending piece group such that the third contact surfaces and a distal-most position of the bending piece group are in rotatably contact with each other.

10 Claims, 12 Drawing Sheets

(51) Int. Cl.
 *A61B 1/005* (2006.01)
 *A61B 1/018* (2006.01)
(52) U.S. Cl.
 CPC ...... *A61B 1/00117* (2013.01); *A61B 1/00128* (2013.01); *A61B 1/018* (2013.01)

(56) References Cited

U.S. PATENT DOCUMENTS

| | | | | |
|---|---|---|---|---|
| 2003/0036748 | A1* | 2/2003 | Cooper | A61B 34/30 606/1 |
| 2005/0131279 | A1* | 6/2005 | Boulais | A61B 1/0052 600/141 |
| 2006/0173243 | A1* | 8/2006 | Watanabe | A61B 1/018 600/141 |
| 2010/0004509 | A1* | 1/2010 | Naito | A61B 1/00133 600/141 |
| 2014/0378767 | A1* | 12/2014 | Lee | A61B 1/0057 600/141 |
| 2015/0230692 | A1* | 8/2015 | Matsuda | A61B 1/005 600/104 |

* cited by examiner

BENDING PORTION OF ENDOSCOPE AND ENDOSCOPE

CROSS REFERENCE TO RELATED APPLICATION

This application is a continuation application of PCT/JP2017/033405 filed on Sep. 15, 2017 and claims benefit of Japanese Application No. 2017-028775 filed in Japan on Feb. 20, 2017, the entire contents of which are incorporated herein by this reference.

BACKGROUND OF INVENTION

1. Field of the Invention

The present invention relates to a bending portion of an endoscope, which is formed by a plurality of bending pieces provided continuously along a longitudinal direction, and to an endoscope.

2. Description of the Related Art

In recent years, endoscopes have been widely used in medical fields and industrial fields. Such endoscopes are provided with a rigid distal end portion at the distal-most part of an elongated insertion portion. The distal end portion includes an image pickup unit for picking up an image of an observation site, an illumination optical system for radiating illumination light to the observation site, and the like.

In addition, the insertion portion includes, at the proximal end side of the distal end portion, a bending portion for changing the direction of the distal end portion in any direction. In general, a bending portion includes a bending piece set. The bending piece set includes a plurality of bending pieces disposed along the longitudinal direction of the insertion portion, and the respective bending pieces adjacent to each other are coupled with rivets and the like to form a main part of the bending portion.

On the other hand, in endoscopes of a kind that requires diameter reduction in particular, a technique is known in which, instead of the above-described bending pieces, a rivetless bending piece group (joint ring group) including a plurality of bending pieces (joint rings) that are overlapped in series along the longitudinal axis direction is employed in the bending portion, as disclosed in Japanese Patent Application Laid-Open Publication No. 2005-7068, for example. According to the technology disclosed in the Japanese Patent Application Laid-Open Publication No. 2005-7068, each of the joint rings includes: a raised portion on a first end surface located on one end side of each of the joint rings; a receiving portion with which a raised portion of another adjacent joint ring is in contact, on a second end surface located on another end side of each of the joint rings; and a restricting portion provided on the receiving portion, for restricting the rotation of the adjacent joint ring in axial direction, to thereby restrict torsion of the bending portion. Furthermore, according to the technology disclosed in the Japanese Patent Application Laid-Open Publication No. 2005-7068, the outer circumference of the bending piece group is covered with a braid formed in a mesh tube made of extra-fine stainless wire rods, to more surely prevent the torsion of the bending tube.

Incidentally, in the bending portion of the endoscope, which includes the above-described bending piece group, a braid covering the outer circumferential portion of the bending piece group is being considered to be omitted for the purpose of further reducing the diameter and simplifying the structure of the endoscope.

SUMMARY OF THE INVENTION

A bending portion of an endoscope according to one aspect of the present invention is a bending portion including: a bending piece group that includes a plurality of first bending pieces, each of the first bending pieces including first contact surfaces formed on a proximal end surface of the each of the first bending pieces and second contact surfaces formed on the distal end surface of the each of the first bending pieces, the first and second contact surfaces facing a direction of a longitudinal axis of an insertion portion, each of the first bending pieces including inside a first insertion portion for allowing insertion of internal components along the longitudinal axis, the bending piece group being provided along the longitudinal axis such that the first contact surfaces and the second contact surfaces of the first bending pieces adjacent to each other are rotatably in contact with each other; a second bending piece including coupling portions on a distal end side of the second bending piece, and third contact surfaces on a proximal end side of the second bending piece, the coupling portions being for coupling the second bending piece to a frame member constituting a distal end portion of the insertion portion such that the second bending piece resists torsion about the longitudinal axis, the third contact surfaces facing the direction of the longitudinal axis, the second bending piece including a second insertion portion for allowing insertion of the internal components, the second insertion portion being formed in the second bending piece so as to be coincident with the first insertion portion on a same projection plane, the second bending piece being interposed between the frame member and the bending piece group such that the third contact surfaces and the second contact surfaces of the first bending piece located at a distal-most position of the bending piece group are rotatably in contact with each other; and a plurality of internal components, distal end portions of which are fixed to respective fixed positions of the frame member, the plurality of internal components being inserted inside the second bending piece and the bending piece group. The coupling portions are coupled to the frame member through rivets so as to be rotatable about an axis in a direction orthogonal to the longitudinal axis, the rivets are arranged at positions shifted by 90 degrees about the longitudinal axis with respect to the direction in which the third contact surfaces are provided, and when the plurality of internal components are projected in the direction of the longitudinal axis, arrangement of the plurality of internal components are corrected from the respective fixed positions to arrangement defined by regions of the second insertion portion formed inside of the second bending piece.

In addition, an endoscope according to one aspect of the present invention includes the bending portion.

DETAILED DESCRIPTION OF THE PREFERRED EMBODIMENT(S)

Figure 1:
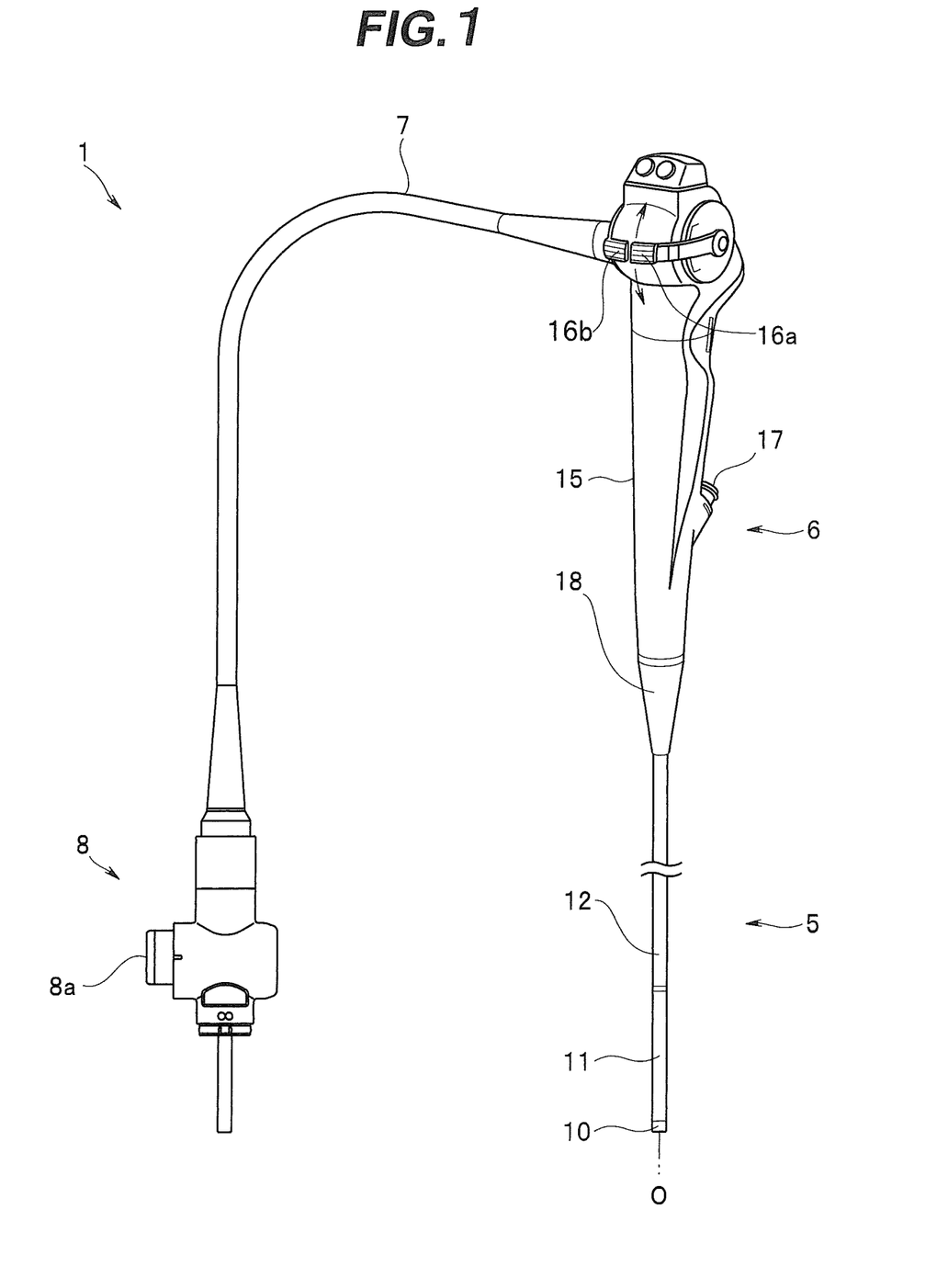
FIG. 1 is a perspective view illustrating an appearance of an endoscope.
Figure 2:
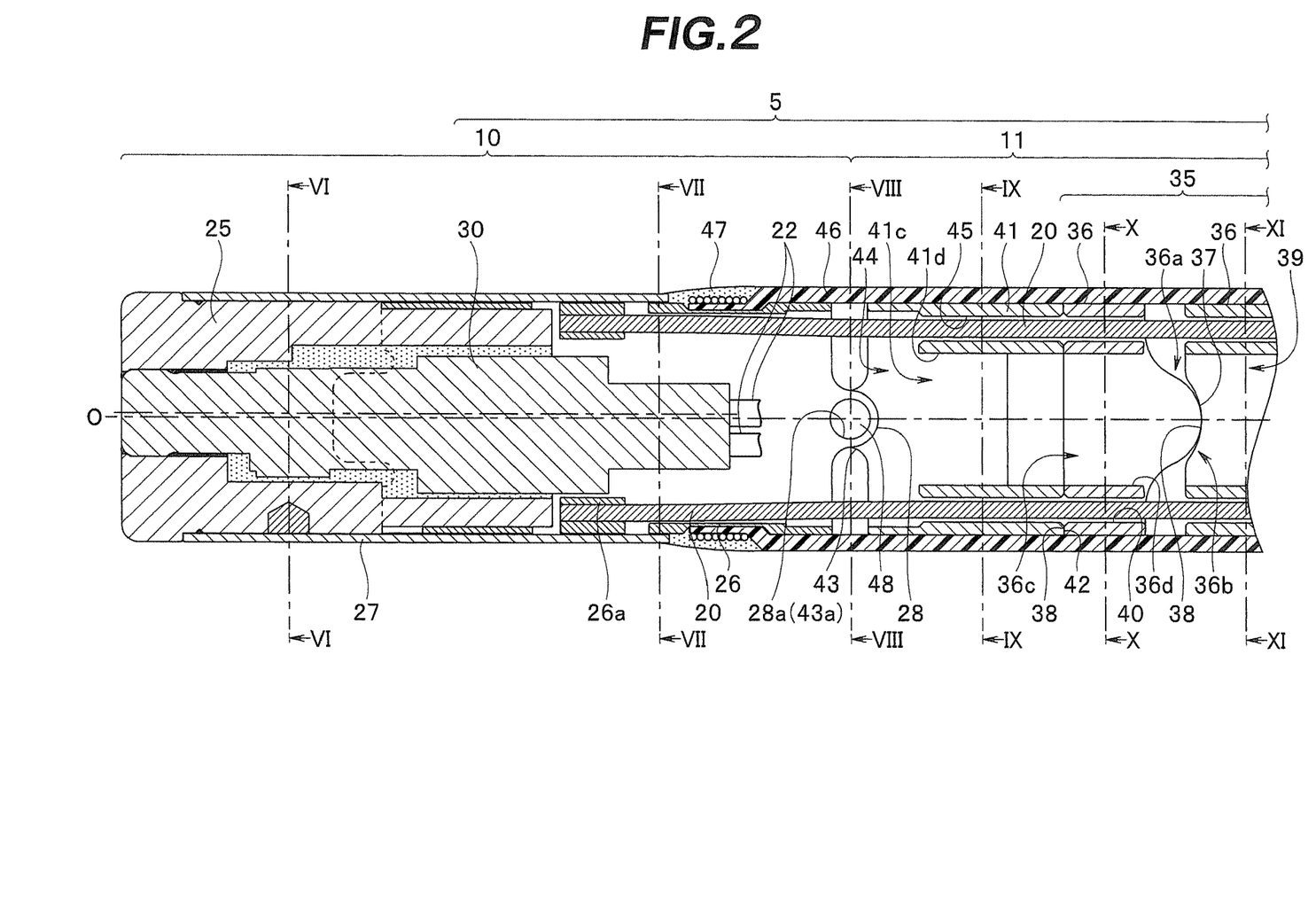
FIG. 2 is a cross-sectional view of main parts of a distal end portion and a bending portion, taken along the II-II line in FIG. 6.
Figure 3:
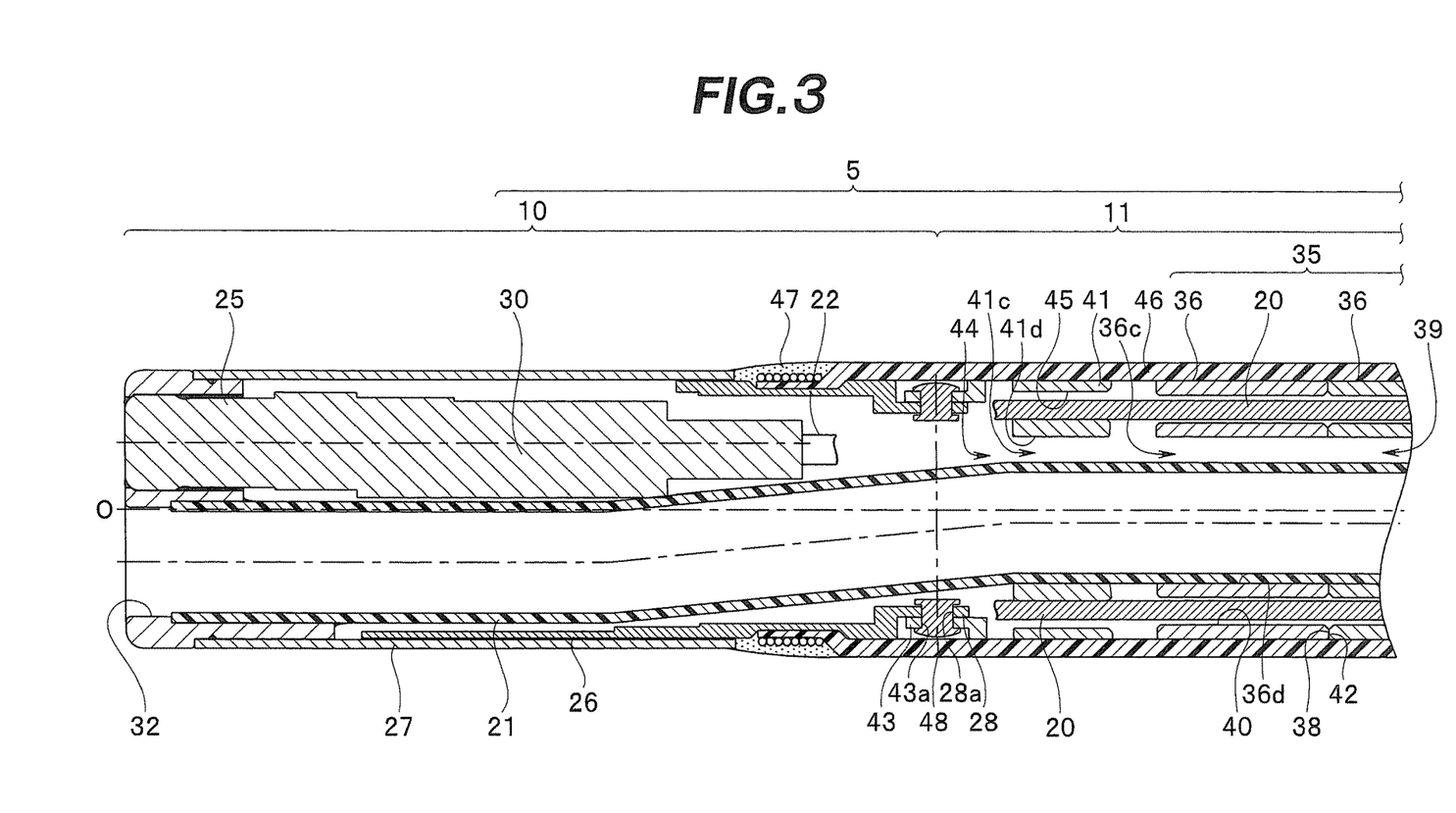
FIG. 3 is a cross-sectional view of the main parts of the distal end portion and the bending portion, taken along the line III-III in FIG. 6.
Figure 4:
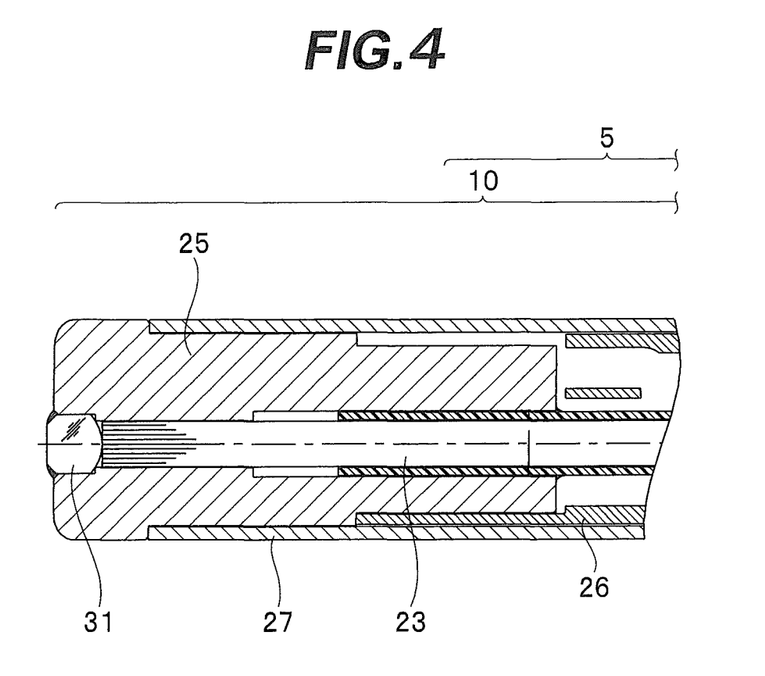
FIG. 4 is a cross-sectional view of the main part of the distal end portion taken along the IV-IV line in FIG. 6.
Figure 5:
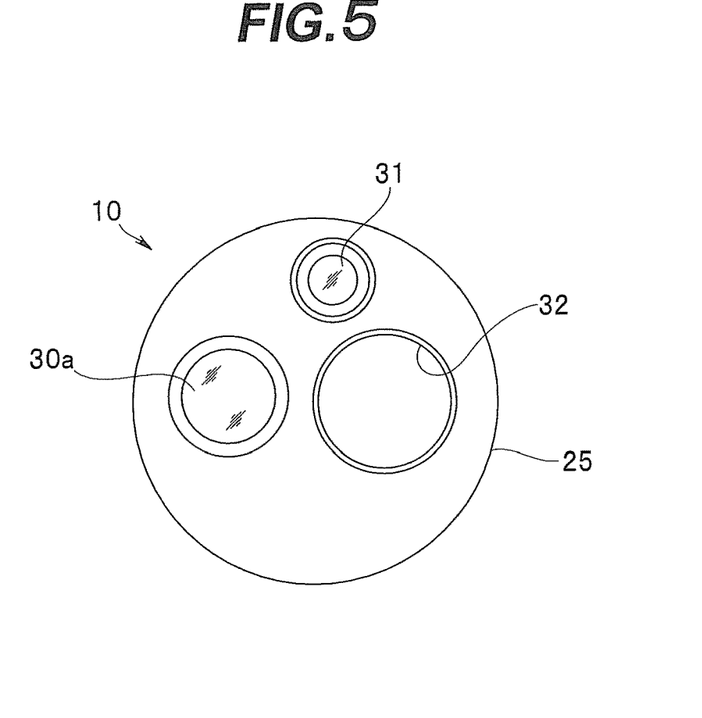
FIG. 5 is an end view of the distal end portion.
Figure 6:
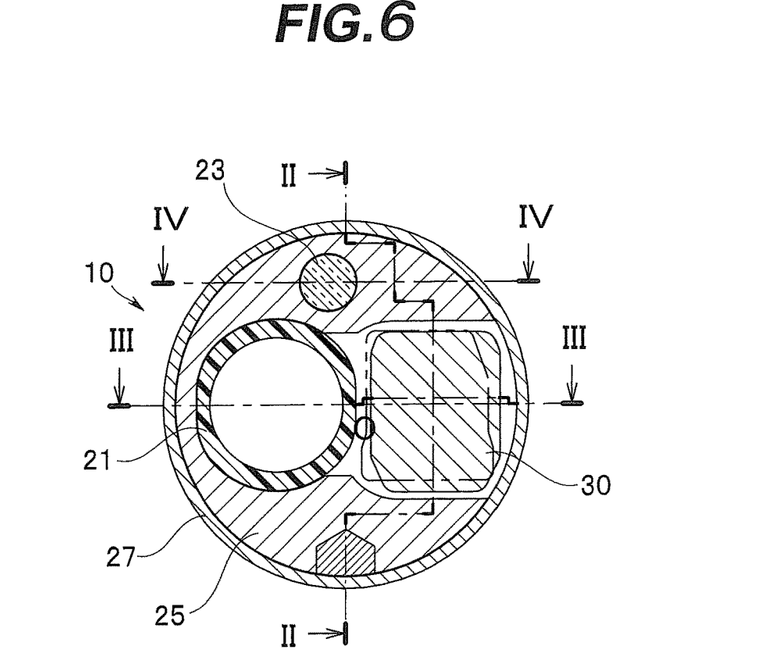
FIG. 6 is a cross-sectional view of the distal end portion taken along the VI-VI line in FIG. 2.
Figure 7:
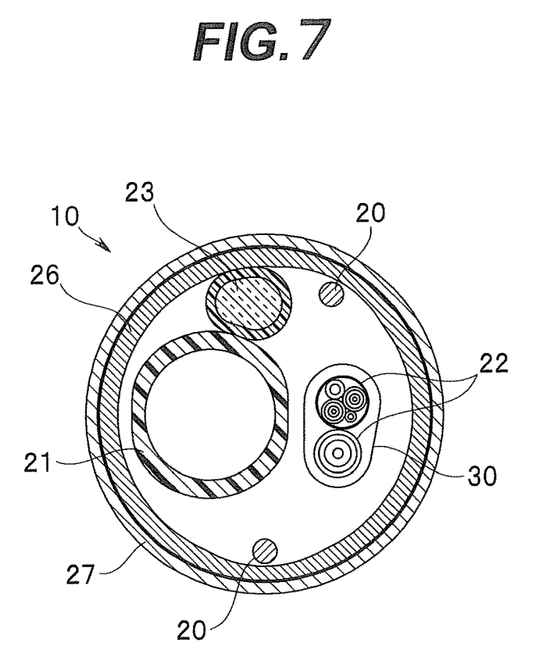
FIG. 7 is a cross-sectional view of the distal end portion taken along the VII-VII line in FIG. 2.
Figure 8:
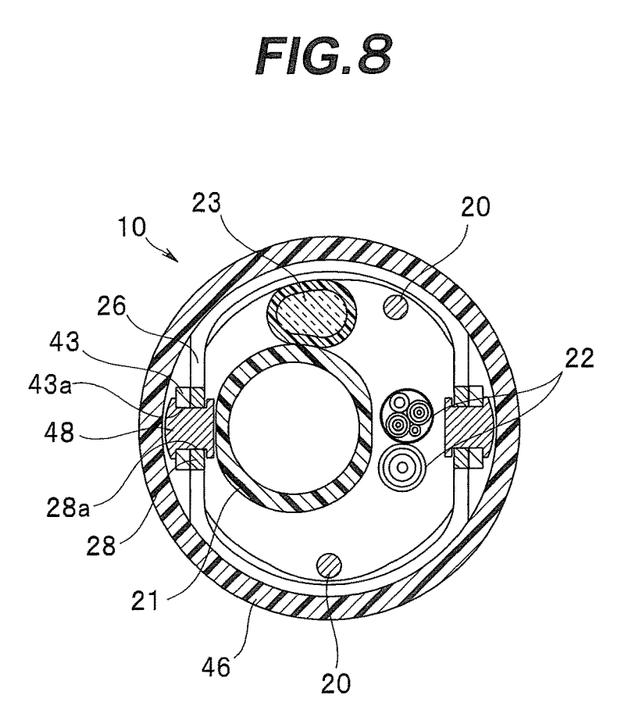
FIG. 8 is a cross-sectional view of a coupling portion between the distal end portion and the bending portion, taken along the VIII-VIII line in FIG. 2.
Figure 9:
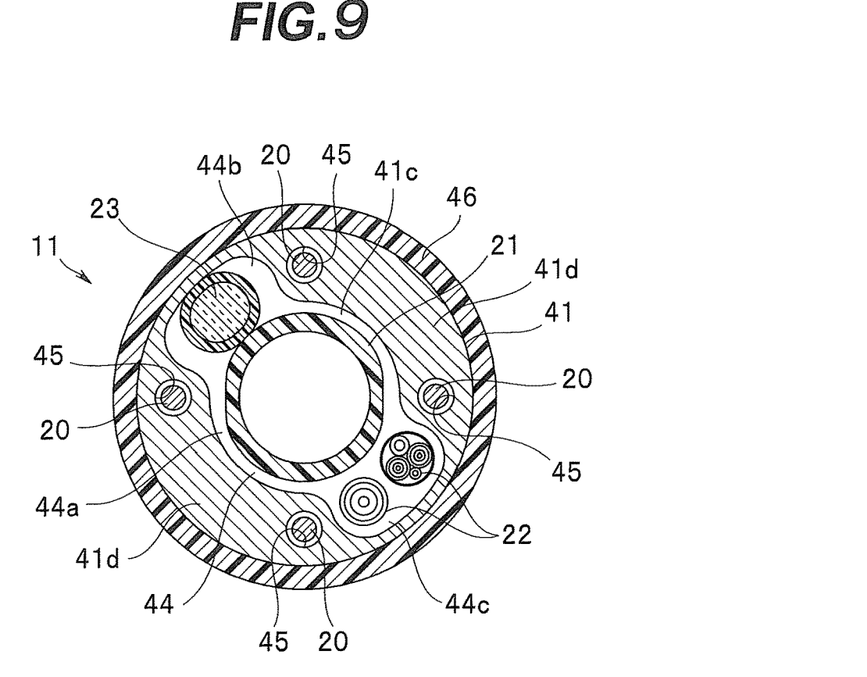
FIG. 9 is a cross-sectional view of the bending portion taken along the IXI-IX line in FIG. 2.
Figure 10:
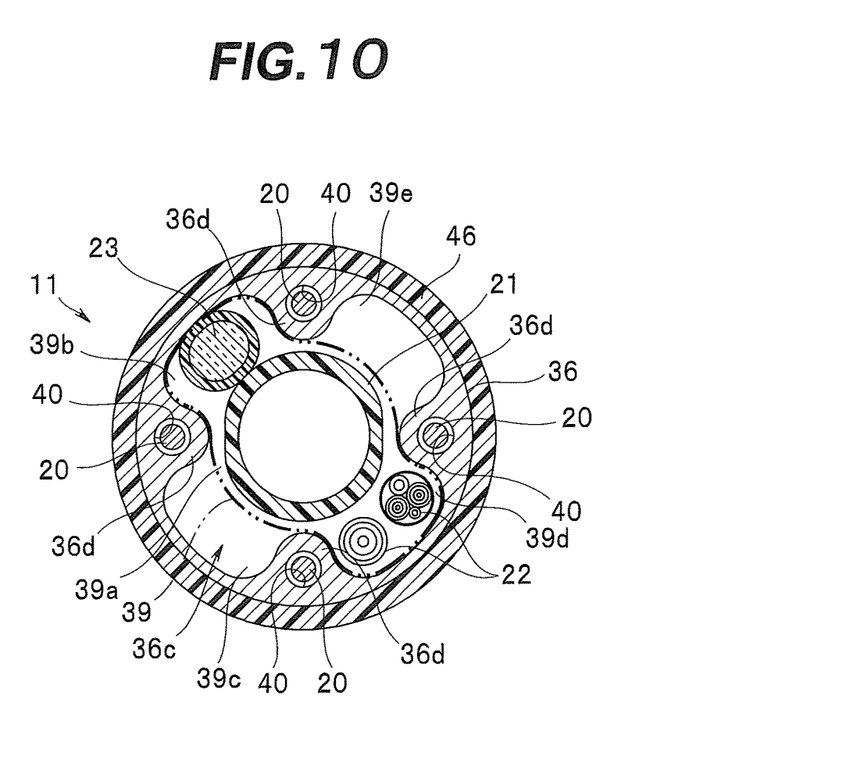
FIG. 10 is a cross-sectional view of the bending portion taken along the X-X line in FIG. 2.
Figure 11:
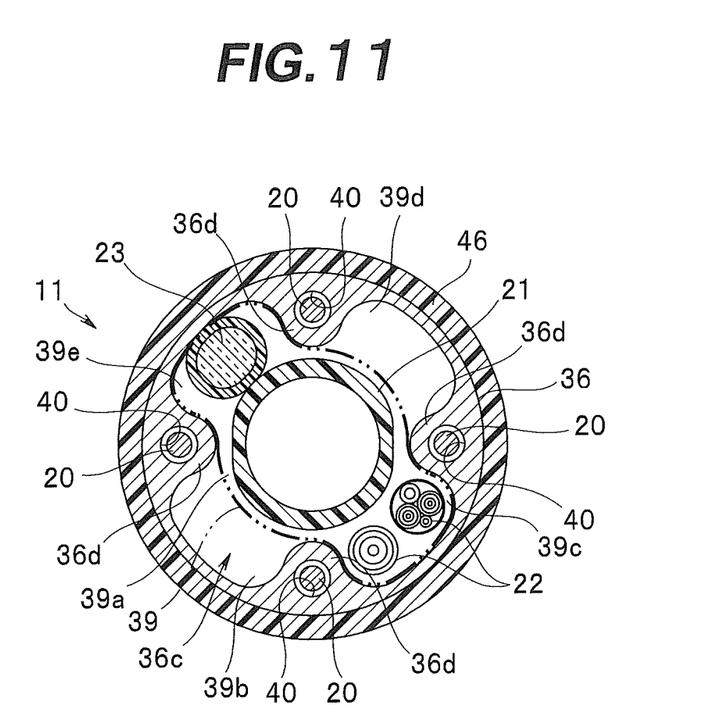
FIG. 11 is a cross-sectional view of the bending portion taken along the XI-XI line in FIG. 2.
Figure 12:
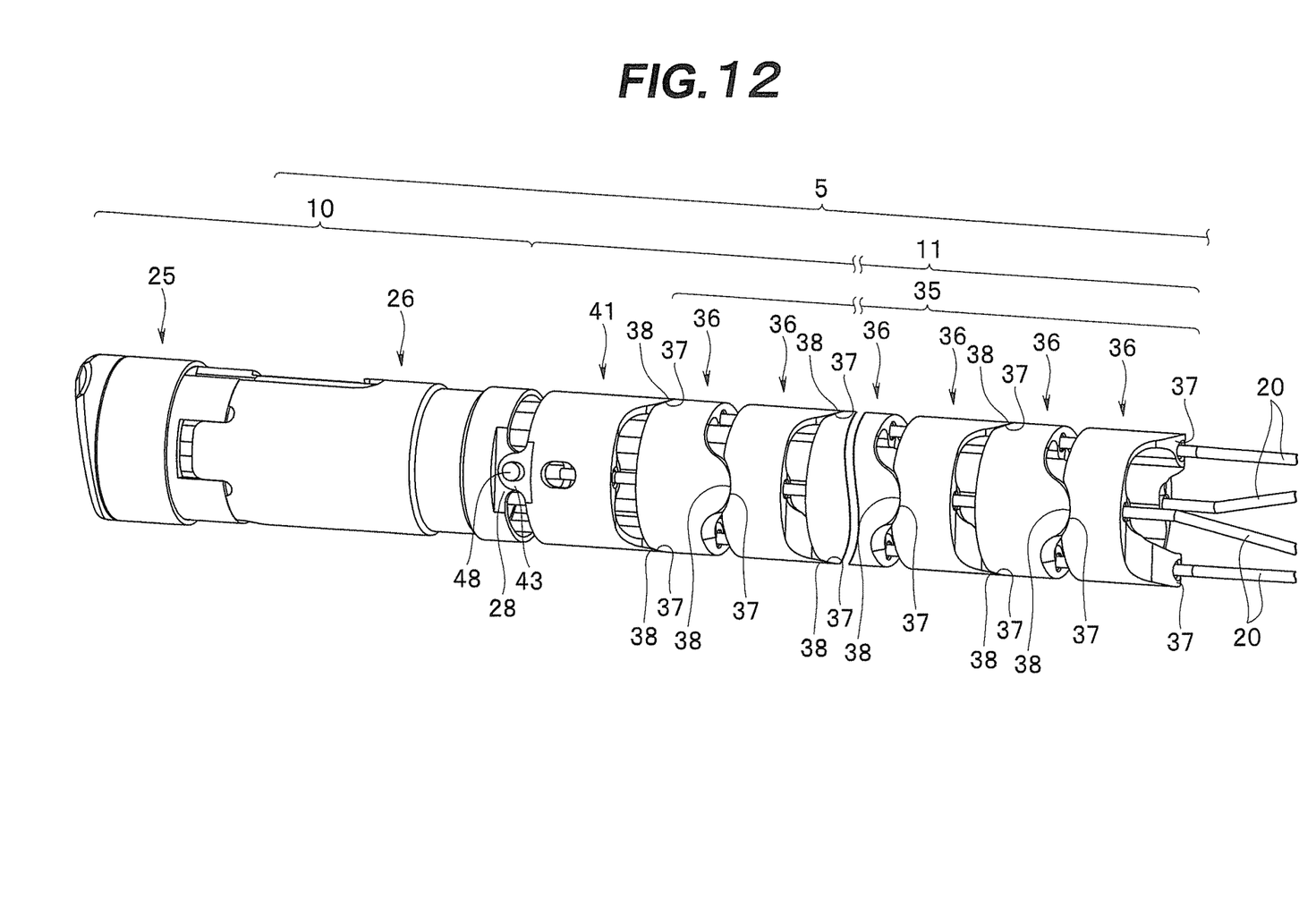
FIG. 12 is a perspective view illustrating internal structures of the distal end portion and the bending portion.
Figure 13:
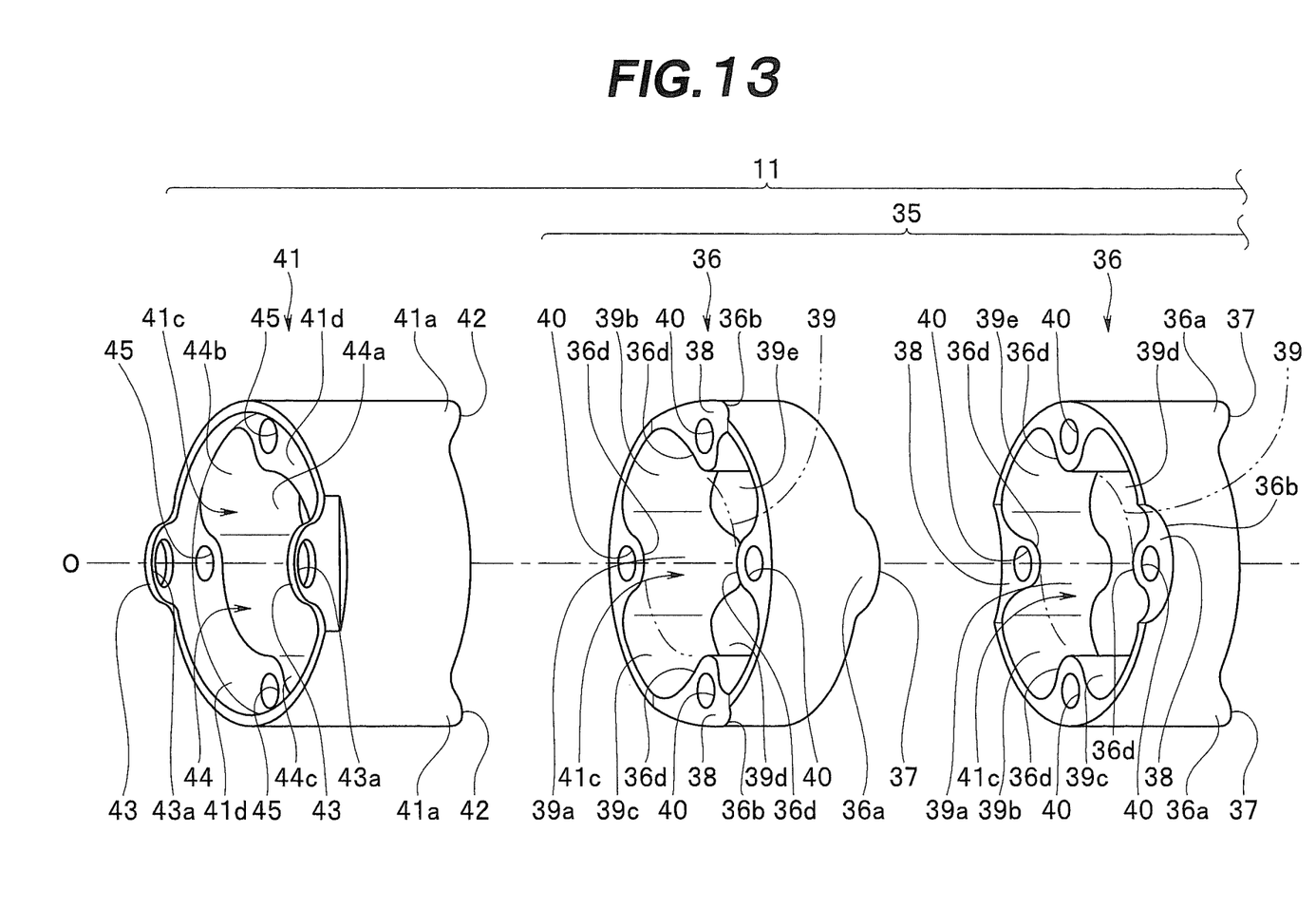
FIG. 13 is an exploded perspective view illustrating a relation between first bending pieces and a second bending piece.

Hereinafter, an embodiment of the present invention will be described with reference to drawings. The drawings relates to an embodiment of the present invention: FIG. 1 is a perspective view illustrating an appearance of an endoscope; FIG. 2 is a cross-sectional view of main parts of a distal end portion and a bending portion, taken along the II-II line in FIG. 6; FIG. 3 is a cross-sectional view of the main parts of the distal end portion and the bending portion, taken along the III-III line in FIG. 6; FIG. 4 is a cross-sectional view illustrating the main part of the distal end portion, taken along the IV-IV line in FIG. 6; FIG. 5 is an end view of the distal end portion; FIG. 6 is a cross-sectional view of the distal end portion taken along the VI-VI line in FIG. 2; FIG. 7 is a cross-sectional view of the distal end portion taken along the VII-VII line in FIG. 2; FIG. 8 is a cross-sectional view of a coupling portion between the distal end portion and the bending portion, taken along the VIII-VIII line in FIG. 2; FIG. 9 is a cross-sectional view of the bending portion taken along the IXI-IX line in FIG. 2; FIG. 10 is a cross-sectional view of the bending portion taken along the X-X line in FIG. 2; FIG. 11 is a cross-sectional view of the bending portion taken along the XI-XI line in FIG. 2; FIG. 12 is a perspective view illustrating internal structures of the distal end portion and the bending portion; and FIG. 13 is an exploded perspective view illustrating a relation between first bending pieces and a second bending piece.

An endoscope 1 shown in FIG. 1 includes an elongated and flexible insertion portion 5, an operation portion 6 provided continuously with the proximal end side of the insertion portion 5, and a universal cable 7 extended from the operation portion 6. The endoscope 1 according to the present embodiment is an endoscope for renal pelvis/urinary organs, for example. The outer diameter of the insertion portion 5 is formed to be extremely thin, about several millimeters.

The insertion portion 5 includes a main part configured by including in the following order from the distal end side: a rigid distal end portion 10; a bending portion 11 bendable in four directions, i.e., up, down, left, and right directions; and a pliable flexible tube portion 12 having flexibility, for example. The up, down, left, and right directions in the present embodiment are defined so as to correspond to the up, down, left, and right directions of an endoscopic image picked up by an image pickup unit to be described later.

The operation portion 6 includes a grasping portion 15, a pair of bending operation levers 16a, 16b, a treatment instrument insertion port 17, and a breaking-prevention portion 18.

The grasping portion 15 is made of an exterior member configured to be graspable by a user, and includes a space for housing inside thereof various kinds of internal components.

The bending operation lever 16a is operated and rotated in preset two directions with respect to a neutral position, to cause a pair of pulling wires 20 (see FIG. 12) to be pulled or relaxed, to thereby enable the bending portion 11 to bend in an up direction or a down direction. Similarly, the bending operation lever 16b is operated and rotated in preset two directions with respect to the neutral position, to cause a pair of pulling wires 20 to be pulled or relaxed, to thereby enable the bending portion 11 to bend in a right direction or a left direction.

The treatment instrument insertion port 17 is in communication with the proximal end side of a treatment instrument insertion channel 21 (see FIG. 3) that is inserted in the insertion portion 5 and operation portion 6.

The universal cable 7 is a composite cable in which a video signal cable 22 (see FIGS. 2, 3) and a light guide cable 23 (see FIG. 4) that are inserted through the insertion portion 5 and operation portion 6 are inserted. A light source connector 8 is provided at the extension end portion of the universal cable 7. The light source connector 8 is configured to be attachable to and detachable from a light source apparatus, not illustrated. In addition, the light source connector 8 includes a connector portion 8a configured to be detachably connected to a video processor, not illustrated, through a signal cable not illustrated.

As shown in FIGS. 2 to 4, the distal end portion 10 includes inside thereof a metallic distal end rigid portion 25.

The distal end rigid portion 25 holds an image pickup unit 30 including an objective optical system 30a (see FIG. 5). The image pickup unit 30 incorporates an image pickup device (not illustrated) such as CCD, CMOS, etc., for picking up an optical image passed through the objective optical system 30a. In addition, the proximal end side of the image pickup unit 30 is connected with the distal end side of the video signal cable 22 that is one of the internal components inserted through the insertion portion 5. That is, the distal end rigid portion 25 holds the distal end side of the video signal cable 22 through the image pickup unit 30.

In addition, the distal end rigid portion 25 holds inside thereof the distal end side of the light guide cable 23 integrally with an illumination optical system 31, the light guide cable 23 being one of the internal components inserted through the insertion portion 5.

Furthermore, a channel hole 32 is open on the distal end rigid portion 25, and channel hole 32 holds the distal end side of the treatment instrument insertion channel 21 that is one of the internal components inserted through the insertion portion 5.

As shown in FIGS. 2 to 5, for example, the image pickup unit 30 is connected to the distal end of the video signal cable 22 in the distal end portion 10. In the distal end portion 10, in order to effectively arrange the image pickup unit 30 of a relatively large size together with the treatment instrument insertion channel 21, the image pickup unit 30 and the treatment instrument insertion channel 21 are arranged side by side along the diameter direction. In addition, the illumination optical system 31 and the light guide cable 23 are arranged in the space upper than the image pickup unit 30 and the treatment instrument insertion channel 21. Thus, a predetermined arrangement is set in the distal end portion 10 so that various kinds of internal components are effectively held in the narrow space in the distal end portion 10.

A metallic coupling frame 26 that is coupled to the bending portion 11 is provided on the proximal end side of the distal end rigid portion 25. The coupling frame 26 is provided with a pair of coupling protruding portions 28 protruding toward the proximal end side. The coupling protruding portions 28 are respectively arranged at positions that are 180-degree rotationally symmetric about the longitudinal axis O of the insertion portion 5. More specifically, in the present embodiment, the coupling protruding portions 28 are arranged forming a pair in the left/right direction of the insertion portion 5 so as to be opposed to each other. The coupling protruding portions 28 are respectively provided with shaft holes 28a opposed to each other in a direction orthogonal to the longitudinal axis O.

Furthermore, the outer circumferences of the distal end rigid portion 25 and the coupling frame 26 are covered with a metallic exterior tube 27 formed in a substantially cylindrical shape.

Note that, in the present embodiment, the distal end rigid portion 25, the coupling frame 26, and the exterior tube 27 are configured as a frame member that constitutes the distal end portion 10.

As shown in FIGS. 2, 3, 12, and 13, the bending portion 11 includes a bending piece group 35 composed of a plurality of first bending pieces 36. Each of the first bending pieces 36 is made of a metallic ring-shaped member.

Each of the first bending pieces 36 includes, on the proximal end side surface thereof, a pair of first contact surfaces 37 that face the direction of the longitudinal axis O of the insertion portion 5. Specifically, each of the first bending pieces 36 includes, on the proximal end side thereof, the protruding portions 36a provided respectively at the positions that are 180-degree rotationally symmetric about the longitudinal axis O. The pair of protruding portions 36a respectively form protruding surfaces on the proximal end surface of each of the first bending pieces 36, and the respective protruding surfaces are set as the first contact surfaces 37.

In addition, each of the first bending pieces 36 includes, on the distal end surface thereof, a pair of second contact surfaces 38 that face the direction of the longitudinal axis O of the insertion portion 5. Specifically, each of the first bending pieces 36 includes, on the distal end side thereof, recessed portions 36b at positions shifted with respect to the respective protruding portions 36a by 90 degrees about the longitudinal axis O, the positions being 180-degree rotationally symmetric about the longitudinal axis O. The pair of recessed portions 36b respectively form recessed surfaces on the distal end surface of each of the first bending pieces 36, and the respective recessed surfaces are set as the second contact surfaces 38.

Each of the first bending pieces 36 includes inside thereof a through hole 36c penetrating each of the first bending pieces 36 in the direction of the longitudinal axis O of the insertion portion 5.

Furthermore, each of the first bending pieces 36 includes, inside thereof, thick portions 36d protruding toward the inside of the through hole 36c. The thick portions 36d are formed at symmetric positions that correspond to the positions of the first contact surfaces 37 and the second contact surfaces 38 so as to be respectively located at 90-degree rotation positions, for example. In such a configuration, a center region 39a surrounded by protruding end portions of the respective thick portions 36d is formed in the through hole 36c. Inside the through hole 36c, first to fourth small regions 39b to 39e that are surrounded by side portions of the respective thick portions 36d are formed around the center region 39a at the symmetric positions so as to be located respectively at 90-degree rotation positions. Among the respective regions, the center region 39a is a region through which the treatment instrument insertion channel 21 is insertable, for example. The treatment instrument insertion channel 21 is the internal component having the largest diameter among the internal components inserted through the bending portion 11. The first to fourth small regions 39b to 39e are regions through which the video signal cable 22 or the light guide cable 23 is arbitrarily insertable. The video signal cable 22 and the light guide cable 23 are the internal components having smaller diameters than the diameter of the treatment instrument insertion channel 21.

Each of the thick portions 36d includes a wire insertion hole 40 penetrating through each of the thick portions 36 in the direction of the longitudinal axis O.

The plurality of first bending pieces 36, each of which is thus configured, are aligned in line, with the first bending pieces adjacent to each other being shifted from each other by 90 degrees about the longitudinal axis O. In such a configuration, the first contact surfaces 37 and the second contact surfaces 38 of the first bending pieces 36, 36 adjacent to each other are respectively in contact with each other such that the first bending pieces are rotatable about an axis in the direction orthogonal to the longitudinal axis O, to form a bending piece group 35 including a series of the plurality of first bending pieces 36 provided continuously along the direction of the longitudinal axis O (see FIG. 12). In addition, rotation pairs at which the first contact surfaces 37 and the second contact surfaces 38 are respectively in contact with each other are formed at positions alternately shifted about the longitudinal axis O, which enables the bending piece group 35 to bend in the up and down directions and in the left and right directions.

In such a configuration, a first insertion portion 39 through which the various kinds of internal components are insertable along the direction of the longitudinal axis O is formed in each of the first bending pieces 36 by combining, among the respective regions formed in the through hole 36c, the center region 39a and a pair of regions formed by the first and third small regions 39b, 39d opposed to each other across the center region 39a or combining, among the respective regions formed in the through hole 36c, the center region 39a and a pair of regions formed by the second and fourth regions 39c, 39e opposed to each other across the center region 39a (see FIGS. 10, 11).

In addition, in the bending portion 11, a second bending piece 41 made of a metallic ring-shaped member is provided continuously with the distal end of the above-described bending piece group 35.

The second bending piece 41 includes, on the proximal end surface thereof, a pair of third contact surfaces 42 facing the direction of the longitudinal axis O of the insertion portion 5. Specifically, the second bending piece 41 includes, on the proximal end side thereof, protruding portions 41a at the positions that are 180-degree rotationally symmetric about the longitudinal axis O. The pair of protruding portions 41a respectively form protruding surfaces on the proximal end surface of the second bending piece 41, and the respective protruding surfaces are set as the third contact surfaces 42.

In addition, the second bending piece 41 includes, on the distal end side thereof, a pair of coupling protruding portions 43, which protrude toward the distal end side, as coupling portions. The coupling protruding portions 43 are arranged at positions shifted with respect to the respective protruding portions 41a by 90 degrees about the longitudinal axis O of the insertion portion 5, the positions being 180-degree rotationally symmetric about the longitudinal axis O. More specifically, in the present embodiment, the respective coupling protruding portions 43 are arranged forming a pair in the left/right direction of the insertion portion 5 so as to correspond to the respective coupling protruding portions 28 provided to the coupling frame 26 of the distal end portion 10. In addition, the coupling protruding portions 43 are respectively provided with shaft holes 43a opposed to each other in the direction orthogonal to the longitudinal axis O.

The second bending piece 41 includes inside thereof a through hole 41c penetrating the second bending piece in the direction of the longitudinal axis O of the insertion portion 5.

Furthermore, the second bending piece 41 includes inside thereof a pair of thick portions 41d formed in a substantially partial arc shape and protruding toward the inner side of the through hole 41c.

Inside the through hole 41c, a second insertion portion 44 through which the various kinds of internal components are inserted is formed by the thick portions 41d. The second insertion portion 44 is formed so as to be coincident with the first insertion portion 39 on a same projection plane in the direction of the longitudinal axis O. That is, inside the through hole 41c, a center region 44a surrounded by protruding end portions of the respective thick portions 41d is formed. Furthermore, inside the through hole 41c, first and second small regions 44b, 44c that are surrounded by side portions of the respective thick portions 41d are formed around the center region 44a at positions that are 180-degree rotationally symmetric. Among these regions, the center region 44a is a region through which the treatment instrument insertion channel 21 is insertable, for example. The treatment instrument insertion channel is the internal component having the largest diameter among the internal components inserted through the bending portion 11. The first and second small regions 44b, 44c are regions through which the video signal cable 22 or the light guide cable 23 is arbitrarily insertable. The video signal cable 22 and the light guide cable 23 are the internal components having smaller diameters than the diameter of the treatment instrument insertion channel 21.

In addition, the thick portions 41d respectively include a pair of wire insertion holes 45 that penetrate the thick portions in the direction of the longitudinal axis O.

The second bending piece 41 thus configured is interposed between the distal end portion 10 and the bending piece group 35.

That is, as shown in FIGS. 2, 3, for example, the distal end side of the second bending piece 41 is coupled to the coupling frame 26 by the coupling protruding portions 43 being coupled to the coupling protruding portions 28 using rivets. More specifically, the shaft holes 43a of the coupling protruding portions 43 provided on the distal end side of the second bending piece 41 and the shaft holes 28a of the coupling protruding portions 28 provided on the proximal end side of the coupling frame 26 are coupled to each other through rivets 48, and thereby the second bending piece 41 is coupled to the coupling frame 26 of the distal end portion 10 so as to be rotatable around the axis in the direction orthogonal to the longitudinal axis O and resist the torsion about the longitudinal axis O.

On the other hand, the proximal end side of the second bending piece 41 is connected to the bending piece group 35 by the third contact surfaces 42 being in contact with the second contact surfaces 38, which are provided on the distal end side of the first bending piece 36 located at the distalmost position of the bending piece group 35, so as to be rotatable about the axis in the direction orthogonal to the longitudinal axis O.

Thus, the treatment instrument insertion channel 21, the video signal cable 22, and the light guide cable 23, the distal ends of which are fixed to the predetermined positions of the distal end rigid portion 25, are inserted in the second insertion portion 44 of the second bending piece 41 provided continuously with the proximal end side of the distal end portion 10 and in the first insertion portion 39 of the bending piece group 35 (each of the first bending pieces 36).

In such a configuration, as shown in FIGS. 2 to 4, and FIGS. 7 to 9, for example, arrangement of the treatment instrument insertion channel 21, the video signal cable 22, and the light guide cable 23 is corrected in a section from the distal end rigid portion 25 to the second bending piece 41. That is, the second bending piece 41 is fixed to the coupling frame 26 so as to resist torsion, and the second insertion portion 44 is sectionalized into the center region 44a, and the first and second small regions 44b, 44c so as to allow individual insertion of the treatment instrument insertion channel 21, the video signal cable 22, and the light guide cable 23. Therefore, the respective arrangements of the treatment instrument insertion channel 21, the video signal cable 22, and the light guide cable 23 are corrected from the respective arrangements (the respective fixed positions) set in the distal end rigid portion 25 to the arrangements defined by the regions 44a to 44c of the second insertion portion 44.

Then, the treatment instrument insertion channel 21, the video signal cable 22, and the light guide cable 23, the arrangements of which are corrected, are inserted into the first insertion portions 39 formed in the bending piece group 35 (the plurality of first bending pieces 36).

In the configuration, the second insertion portion 44 is formed so as to be coincident with the respective first insertion portions 39 on the same projection plane, which allows the treatment instrument insertion channel 21, the video signal cable 22, and the light guide cable 23, the arrangements of which are corrected by the second insertion portion 44, are inserted into each of the first insertion portions 39 without applying unnecessary stress to each of the first bending pieces 36.

In addition, the pulling wires 20 are inserted in the respective wire insertion holes 40 formed in the respective first bending pieces 36 and in the wire insertion holes 45 formed in the second bending piece 41. The distal ends of the pulling wires 20 are fixed by wire fixing portions 26a (see FIG. 2) provided in the coupling frame 26, which enables the bending portion 11 to bend in conjunction with the rotation operation of the bending operation levers 16a, 16b. That is, the respective pulling wires 20 are pulled or relaxed by the rotation operation of the bending operation levers 16a, 16b, which generates rotation between the first contact surfaces 37 and the second contact surfaces 38, and between the third contact surfaces 42 and the second contact surfaces 38 and enables the bending portion 11 to bend.

Furthermore, the outer circumferences of the second bending piece 41 and the bending piece group 35 (the plurality of first bending pieces 36) are directly covered with an outer cover 46 (without a braid or the like being interposed). A thread-wound adhering portion 47 is provided at the distal end of the outer cover 46, and the thread-wound adhering portion 47 allows the distal end side of the outer cover 46 to be liquid-tightly coupled to the exterior tube 27.

With such an embodiment, the bending portion 11 is configured of the bending piece group 35 and the second bending piece 41. The bending piece group 35 includes the plurality of first bending pieces 36, each of the first bending pieces 36 including, on the proximal end surface thereof, the first contact surfaces 37 and including, on the distal end surface thereof, the second contact surfaces 38, the first contact surfaces 37 and the second contact surfaces 38 facing the direction of the longitudinal axis O of the insertion portion 5, each of the first bending pieces 36 including inside thereof the first insertion portion 39 for allowing insertion of the internal components along the longitudinal axis O, the bending piece group being provided along the longitudinal axis O such that the first contact surfaces 37 and the second contact surfaces 38 of the first bending pieces 36 adjacent to each other are rotatably in contact with each other. The second bending piece 41 includes on the distal end side thereof the coupling protruding portions 43 for coupling the second bending piece 41 to the coupling frame 26 constituting the distal end portion 10 such that the second bending piece resists the torsion about the longitudinal axis O, and the second bending piece 41 includes on the proximal end side thereof the third contact surfaces 42 facing the direction of the longitudinal axis O. The second bending piece 41 further includes inside thereof the second insertion portion 44 for allowing insertion of the internal components, the second insertion portion 44 being formed so as to be coincident with the first insertion portions 39 on the same projection plane, the second bending piece being interposed between the coupling frame 26 and the bending piece group 35 such that the third contact surfaces 42 and the second contact surfaces 38 of the first bending piece 36 located at the distal-most position of the bending piece group 35 are rotatably in contact with each other. Therefore, occurrence of the torsion between the first bending pieces 36 of the bending piece group 35, which are not coupled to each other by rivets and the like, can be surely suppressed by a simple configuration.

That is, the second bending piece 41 that is coupled to the coupling frame 26 so as to resist the torsion about the longitudinal axis O is interposed between the distal end portion 10 and the bending piece group 35, and the second insertion portion 44 for allowing the insertion of the internal components is set so as to be coincident with the respective first insertion portions 39 on the same projection plane. In such a configuration, even if the layout of the respective internal components fixed in the distal end portion 10 is different from the layout of the internal components inserted through each of the first insertion portions 39, the difference in the layouts is corrected by the second insertion portion 44, and then the internal components can be inserted through each of the first insertion portions 39.

Therefore, even when the bending portion 11 is configured by using the bending piece group 35 of a simple configuration without using rivets or the like, the occurrence of the torsion caused by the stress received from the internal components can be suppressed, which leads to an effective diameter size reduction of the bending portion 11.

In addition, the configuration enables the stress received from the internal components to be suppressed. Therefore, the configuration is capable of omitting a braid and the like disposed on the outer circumferences of the bending piece group 35 and other members for preventing the torsion from occurring between the first bending pieces 36 (that is, the outer circumferences of the bending piece group 35 and the other members can be directly covered with the outer cover 46). Such a configuration is capable of achieving the reduction in the diameter of the bending portion 11 more effectively.

Figure 14:
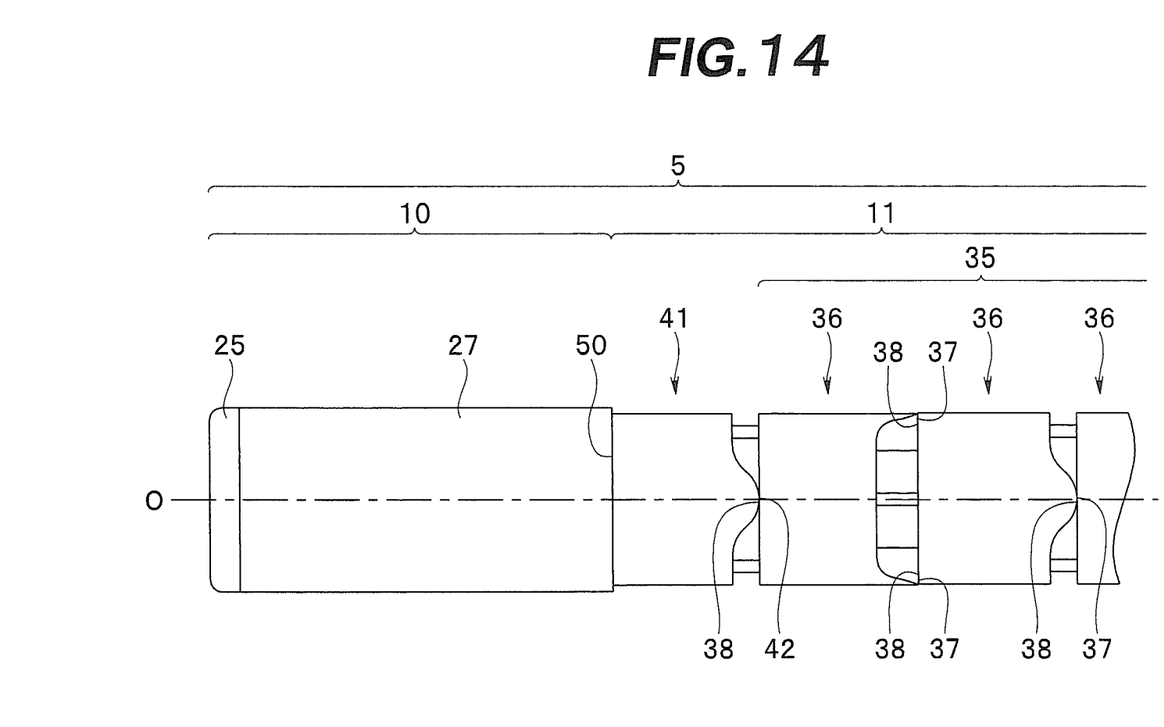
FIG. 14 is a plan view illustrating internal structures of a distal end portion and a bending portion according to a modified example.
Figure 15:
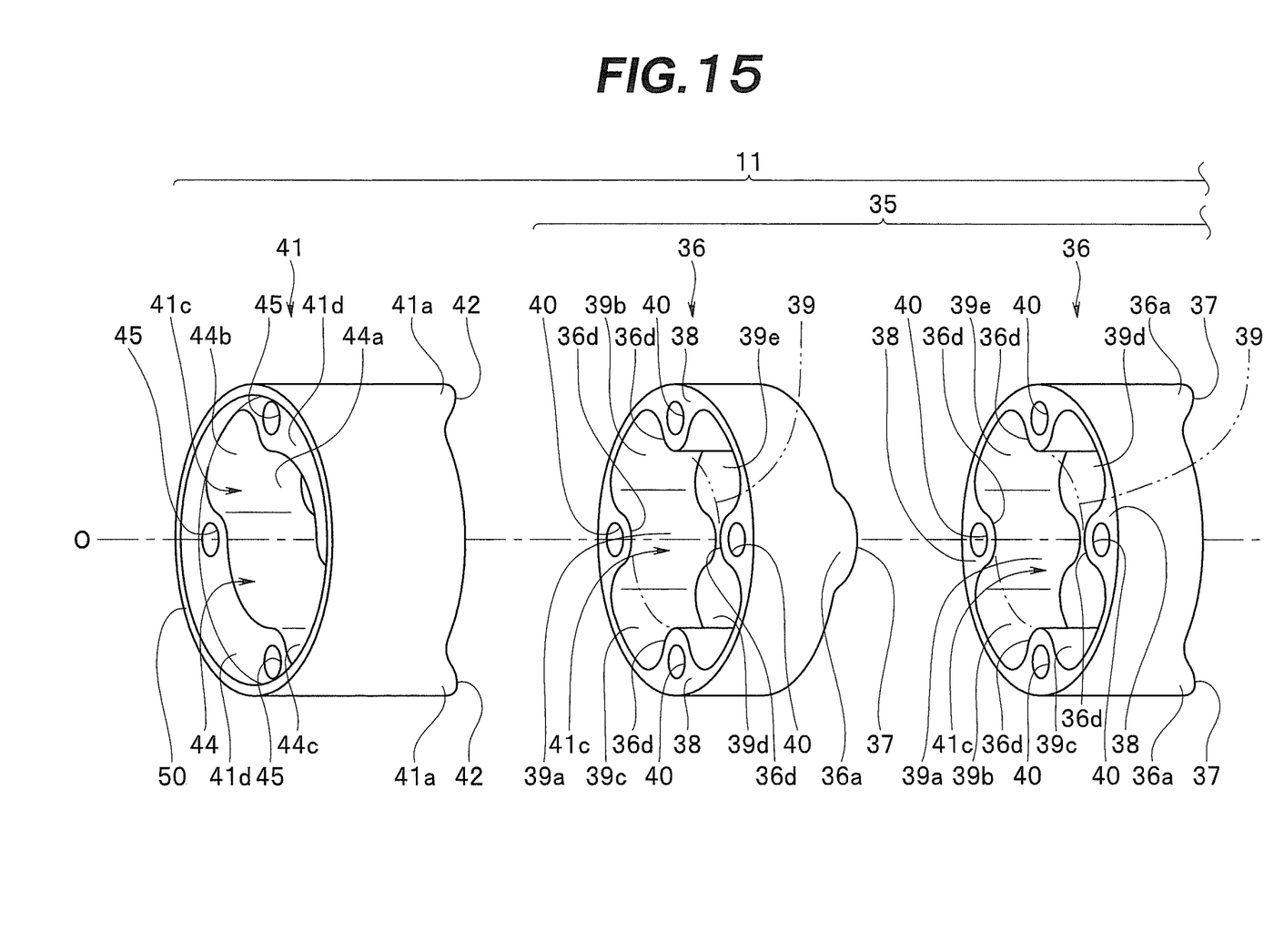
FIG. 15 is an exploded perspective view illustrating a relation between first bending pieces and a second bending piece according to the modified example.

In the present embodiment, as shown in FIGS. 14, 15, for example, the distal end of the second bending piece 41 may be coupled, as a coupling portion 50, to the exterior tube 27 or the like with adhesion or welding. In addition, as shown in the drawings, the flat distal end surface of each of the first bending pieces 36 can be set as-is as the second contact surface 38.

Note that the present invention is not limited to the above-described embodiment and the like, and various modifications and changes are possible. The modifications and changes are also within the technical range of the present invention.

For example, in the above-described embodiment, one example is described in which the bending portion is bendable in four directions, i.e., up and down directions and left and right directions. However, the present invention is not limited to the example, and can be applied to a bending portion of an endoscope, which is bendable in two directions, i.e., up and down directions, or left and right directions.

In addition, the present invention is effective particularly to a bending portion of an endoscope including an insertion portion having a small diameter, such as an endoscope for renal pelvis/urinary organs. However, it is needless to say that the present invention may be applied to a bending portion of another endoscope having a small diameter such as a bronchoscope. Furthermore, it is needless to say that the present invention may be applied to another bending portion of an endoscope including an insertion portion having a diameter equal to or larger than a predetermined diameter.

What is claimed is:

1. An insertion section for an endoscope, the insertion section comprising:
 a frame member;
 a bending piece group comprising a plurality of first bending pieces arranged along a longitudinal axis direction, each of the first bending pieces including first contact surfaces formed on a proximal end surface of each of the first bending pieces and second contact surfaces formed on a distal end surface of each of the first bending pieces, the first and second contact surfaces facing the longitudinal axis direction, each of the first bending pieces having a first opening for allowing insertion of a plurality of internal components along the longitudinal axis direction, the first opening having a first shape in a plane orthogonal to the longitudinal axis direction, the bending piece group being provided along the longitudinal axis direction such that the first contact surfaces and the second contact surfaces of the first bending pieces adjacent to each other are rotatably in contact with each other;
 a second bending piece comprising coupling portions on a distal end side of the second bending piece, and third contact surfaces on a proximal end side of the second bending piece, the coupling portions being configured to couple the second bending piece to the frame member disposed at a distal end portion of the second bending piece such that the second bending piece resists torsion about a longitudinal axis, the third contact surfaces facing the longitudinal axis direction, the second bending piece having a second opening for allowing insertion of the plurality of internal components, the second opening having a second shape in a plane orthogonal to the longitudinal axis direction, the second shape having a second outer contour being aligned with at least a portion of a first outer contour of the first shape when projected in the longitudinal axis direction, the second bending piece connected to the bending piece group such that the third contact surfaces of the second bending piece and the second contact surfaces of the first bending piece located at a distal-most position of the bending piece group are rotatably in contact with each other; and the plurality of internal components extending in the longitudinal axis direction through the first opening of each of the plurality of first bending pieces of the bending piece group, through the second opening of the second bending piece and are fixed to respective fixed positions of the frame member, wherein the coupling portions are coupled to the frame member through rivets so as to be rotatable about an axis in a direction orthogonal to the longitudinal axis, the rivets are arranged at positions shifted by 90 degrees about the longitudinal axis with respect to a direction in which the third contact surfaces are provided, a first arrangement of the plurality of internal components are changed from the respective fixed positions in the frame member to a second arrangement defined by the second shape of the second opening of the second bending piece; and the second arrangement is maintained in the plurality of first bending pieces of the bending piece group by the first shape of the first opening.

2. The insertion portion according to claim 1, further comprising pulling wires having distal ends fixed to the frame member, the pulling wires being inserted through the first bending pieces and the second bending piece, the pulling wires being configured to generate rotation between the first contact surfaces and the second contact surfaces, and between the third contact surfaces and the second contact surfaces, by proximal end sides of the pulling wires being pulled.

3. The insertion portion according to claim 1, further comprising an outer cover that directly covers outer circumferences of the plurality of first bending pieces of the bending piece group and an outer circumference of the second bending piece.

4. The insertion portion according to claim 1, wherein one of the plurality of internal components is one of a treatment instrument insertion channel, a video signal cable, and a light guide cable.

5. The insertion portion according to claim 1, wherein the second opening includes a center region and two side regions each formed radially offset from the center region at symmetric positions with respect to the longitudinal axis, a treatment instrument insertion channel of the plurality of internal components is arranged in the center region, and a video signal cable and a light guide cable of the plurality of internal components are arranged respectively in the two side regions.

6. An endoscope comprising the insertion portion according to claim 1.

7. The insertion portion according to claim 1, wherein each of the two side regions having a smaller size than the center region.

8. An insertion portion for an endoscope, the insertion portion comprising:

the bending section according to claim 1; and the frame member, wherein a fixed arrangement of the plurality of internal components are changed from respective fixed positions in the frame member to the arrangement of the plurality of internal components in the second opening of the second bending piece.

9. An endoscope comprising the insertion portion according to claim 1.

10. A bending section for an insertion portion of an endoscope, the bending section comprising:

a bending piece group extending along a longitudinal axis direction, the bending piece group comprising a plurality of first bending pieces configured to rotate relative to each other about mating contact surfaces, each of the plurality of first bending pieces having a first opening configured to accommodate a plurality of internal components extending along the longitudinal axis direction, the first opening having a first shape in a plane orthogonal to the longitudinal axis direction;

a second bending piece having a proximal end configured to rotate relative to a distal-most first bending piece of the plurality of bending pieces about mating contact surfaces, the second bending piece having a distal end configured to rotate relative to a frame member about rivets connecting the second bending piece and the frame member, the second bending piece having a second opening configured to accommodate the plurality of internal components, the second opening having a second shape in a plane orthogonal to the longitudinal axis direction;

wherein the second shape having a second outer contour being aligned with at least a portion of a first outer contour of the first shape when projected in the longitudinal axis direction such that an arrangement of the plurality of internal components in the first opening of each of the plurality of first bending pieces is the same as an arrangement of the plurality of internal components in the second opening of the second bending piece.

* * * * *